United States Patent
Onishi et al.

(10) Patent No.: US 9,265,454 B2
(45) Date of Patent: Feb. 23, 2016

(54) PUNCTURE NEEDLE AND PUNCTURE DEVICE

(75) Inventors: Syuuichi Onishi, Shizuoka (JP); Mitsuru Jokaji, Yamanashi (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 207 days.

(21) Appl. No.: 13/637,782

(22) PCT Filed: Mar. 16, 2011

(86) PCT No.: PCT/JP2011/056276
§ 371 (c)(1),
(2), (4) Date: Sep. 27, 2012

(87) PCT Pub. No.: WO2011/122350
PCT Pub. Date: Oct. 6, 2011

(65) Prior Publication Data
US 2013/0018405 A1 Jan. 17, 2013

(30) Foreign Application Priority Data
Mar. 30, 2010 (JP) .................... 2010-078886

(51) Int. Cl.
*A61B 5/15* (2006.01)
*A61B 5/151* (2006.01)

(52) U.S. Cl.
CPC ......... *A61B 5/1411* (2013.01); *A61B 5/150022* (2013.01); *A61B 5/15142* (2013.01); *A61B 5/150427* (2013.01); *A61B 5/150519* (2013.01); *A61B 5/1513* (2013.01)

(58) Field of Classification Search
CPC ............. A61B 17/06066; A61B 17/06; A61B 17/3211; A61B 17/0469; A61B 17/0482; A61B 17/06109; A61B 17/32; A61B 2017/06042; A61B 2017/06052; A61B 2017/0464; A61B 2017/00349; A61B 5/1411; A61B 5/150022; A61B 5/150427; A61B 5/150519; A61B 5/15142; A61B 5/1513; A61B 5/150412; A61B 5/145404; A61B 5/150396; A61B 5/150458; A61B 5/150465; A61B 5/150473; B21G 1/006; B21G 1/08
USPC ......... 606/181–185, 172, 167, 223, 170, 222, 606/166, 107; 600/583, 573, 576, 584, 578, 600/574, 564, 567; 604/117, 264, 674, 604/164.01, 272, 239, 6.16, 43, 44, 273, 604/274, 164.12; 206/366; 223/102; 30/164.8, 346.55, 346.57; 81/900, 460, 81/901, 441
See application file for complete search history.

(56) References Cited

U.S. PATENT DOCUMENTS 4,029,319 A 6/1977 Christen
4,468,038 A 8/1984 Saunders
(Continued)

FOREIGN PATENT DOCUMENTS

EP 1695664 A1 8/2006
EP 1977686 A1 10/2008
(Continued)

OTHER PUBLICATIONS

Extended Supplementary European Search Report issued on Jul. 26, 2013 by the European Patent Office in corresponding European Patent Application No. 1172588.9 (7 pages).
International Search Report (PCT/ISA/210) Issued on Apr. 12, 2011, by the Japanese Patent Office as the International Searching Authority for International Application No. PCT/JP2011/056276.

*Primary Examiner* — Jocelin Tanner
(74) *Attorney, Agent, or Firm* — Buchanan Ingersoll & Rooney PC

(57) ABSTRACT

A puncture needle is constituted of a resin material. The puncture needle comprises: an elongated main body having a sharp needlepoint at a distal end thereof; and at least three cutting parts provided so as to project from the elongated main body to a direction perpendicular to a central axis of the elongated main body, extending along the central axis, and arranged around the central axis. Adjacent cutting parts in the three cutting parts are arranged so as to shift to each other in a direction of the central axis, so that the adjacent cutting parts make an incision on a biological surface in a time difference. Further, a height of a distal portion of each cutting part from the central axis is gradually decreased toward a distal direction.

7 Claims, 11 Drawing Sheets

(56) References Cited

U.S. PATENT DOCUMENTS

| | | | |
|---|---|---|---|
| 5,938,679 A | 8/1999 | Freeman et al. | |
| 6,083,238 A | 7/2000 | Alexander, Jr. et al. | |
| 2002/0169426 A1* | 11/2002 | Takagi | 604/272 |
| 2004/0106948 A1* | 6/2004 | Cunningham | 606/223 |
| 2005/0049522 A1 | 3/2005 | Allen | |
| 2005/0089861 A1 | 4/2005 | Allen | |
| 2006/0030789 A1 | 2/2006 | Allen | |
| 2009/0192452 A1* | 7/2009 | Sasajima et al. | 604/99.04 |
| 2009/0216259 A1 | 8/2009 | Sakata et al. | |
| 2010/0049091 A1 | 2/2010 | Haar | |
| 2010/0249650 A1 | 9/2010 | Hikawa et al. | |

FOREIGN PATENT DOCUMENTS

| | | |
|---|---|---|
| JP | 60-45006 U | 3/1985 |
| JP | 2005-334369 A | 12/2005 |
| JP | 2006-34787 A | 2/2006 |
| JP | 2006-512111 A | 4/2006 |
| WO | 85/03857 A1 | 9/1985 |
| WO | WO 2004/041087 A2 | 5/2004 |
| WO | WO 2004/041088 A1 | 5/2004 |
| WO | WO 2007/066772 A1 | 6/2007 |
| WO | 2009044594 A1 | 4/2009 |

* cited by examiner

PUNCTURE NEEDLE AND PUNCTURE DEVICE

TECHNICAL FIELD

The present invention relates to a puncture needle and a puncture device.

BACKGROUND ART

In recent years, accompanying an increase in a number of diabetics, a self monitoring of blood glucose which monitors daily fluctuation of a blood sugar level by a patient himself comes to be recommended.

The measurement of the blood sugar level is carried out by use of a blood glucose monitoring apparatus for automatically measuring an amount of glucose in blood. Prior to the measurement, a patient must sample his own blood.

A method of sampling the blood includes steps of puncturing a skin of a fingertip by a puncture needle and then pressing the vicinity of a punctured portion with fingers or the like to squeeze out the blood.

The puncture to the fingertip is conducted by removably fitting a puncture device having a puncture needle to a puncture apparatus (referred to, for example, Patent Document 1). Specifically, the puncture device is fitted to the puncture apparatus, and the puncture apparatus is operated to project the puncture needle by an operation of a puncture mechanism provided in the puncture apparatus, thereby puncturing the fingertip. Further, a needlepoint of the puncture needle disclosed in the Patent Document 1 is formed into a conical-like shape.

However, when such a needlepoint formed into the conical-like shape is used, depending on conditions such as differences of a skin thickness of a fingertip among individuals, it has empirically been found that it is difficult to sufficiently puncture the fingertip so that the blood flows out from the fingertip. Further, if the needlepoint punctures the fingertip deeply so that the blood reliably flows out from the fingertip, it has also empirically been found that pain is increased.

The Patent Document 1 is JP-A 2005-334369.

DISCLOSURE OF INVENTION

It is an object of the present invention to provide a puncture needle and a puncture device that are capable of reliably puncturing a biological surface to the extent that blood flows out from the biological surface, and can prevent or suppress pain at the time of puncturing with the puncture needle.

In order to attain the above object, there is provided a puncture needle constituted of a resin material. Such a puncture needle comprises: an elongated main body having a sharp needlepoint at a distal end thereof; and at least three cutting parts provided so as to project from the elongated main body to a direction perpendicular to a central axis of the elongated main body, extending along the central axis, and arranged around the central axis, wherein adjacent cutting parts in the three cutting parts are arranged so as to shift to each other in a direction of the central axis, so that the adjacent cutting parts make an incision on a biological surface in a time difference.

In the puncture needle according to the present invention, it is preferred that each of the three cutting parts has a distal portion, wherein a height of the distal portion from the central axis is gradually decreased toward a distal direction thereof.

In the puncture needle according to the present invention, it is also preferred that the at least three cutting parts include an even number of cutting parts, these cutting parts are arranged at equiangular intervals around the central axis, each of the cutting parts has a distal portion, and a height of the distal portion from the central axis is gradually decreased toward a distal direction thereof, wherein the cutting parts include one pair of cutting parts positioned so that they are opposite to each other through the central axis and other pair of cutting parts than the one pair of cutting parts, wherein each of the cutting parts of the one and other pairs has a tip portion, a position of an intersection between lines extended from the tip portions of the one pair of cutting parts toward the distal direction thereof is shifted in the direction of the central axis with respect to a position of an intersection between lines extended from the tip portions of the other pair of cutting parts toward the distal direction thereof.

In the puncture needle according to the present invention, it is also preferred that the cutting parts are arranged at the equiangular intervals around the central axis.

In the puncture needle according to the present invention, it is also preferred that a thickness of a distal portion of each of the cutting parts is gradually decreased toward a distal direction.

In the puncture needle according to the present invention, it is also preferred that each of the cutting parts is continuously formed with the needlepoint.

In the puncture needle according to the present invention, it is also preferred that at least both side surfaces of the distal portion of each cutting part are formed into a plate-like shape.

In the puncture needle according to the present invention, it is also preferred that an angle between the side surfaces is in a range of 10 to 45 degrees.

In order to attain the above object, there is provided a puncture needle having a sharp needlepoint at a distal end thereof and constituted of a resin material. The puncture needle is configured as if two elongated plate-like members each having cutting parts on both longitudinal edges thereof and having a central axis are integrally combined so that their central axes are overlapped with each other to form a common central axis and the elongated plate-like members are arranged about the common central axis so as to have an interval of a predetermined angle therebetween, and wherein distal end portions of the elongated plate-like members are shifted to each other in a direction of the common central axis so that the cutting parts of the one elongated plate-like member and the cutting parts of the other elongated plate-like member make an incision on a biological surface in a time difference.

In the puncture needle according to the present invention, it is preferred that each of the two elongated plate-like members has a distal portion, wherein the width of the distal portion of each elongated plate-like member is gradually decreased toward a distal direction thereof, and wherein the distal portion of at least one of the two elongated plate-like members forms the sharp needlepoint.

In the puncture needle according to the present invention, it is also preferred that the predetermined angle is in a range of 30 to 90 degrees.

In the puncture needle according to the present invention, it is also preferred that a flexural modulus (defined in an ASTMD790) of the resin material is 2000 MPa or more.

In the puncture needle according to the present invention, it is also preferred that a flexural strength (defined in an ASTMD790) of the resin material is 50 MPa or more.

In the puncture needle according to the present invention, it is also preferred that a hardness (Shore R hardness M scale) of the resin material is in a range of 50 to 150.

In the puncture needle according to the present invention, it is also preferred that the resin material is a thermoplastic resin.

In order to attain the above object, there is provided a puncture device comprising: the puncture needle of the present invention; and a casing housing the puncture needle therein so as to be movable.

BEST MODE FOR CARRYING OUT THE INVENTION

Hereinafter, a description will be made on a puncture needle and a puncture device according to the present invention based on preferred embodiments shown in the accompanied drawings in detail.

First Embodiment

Figure 1:
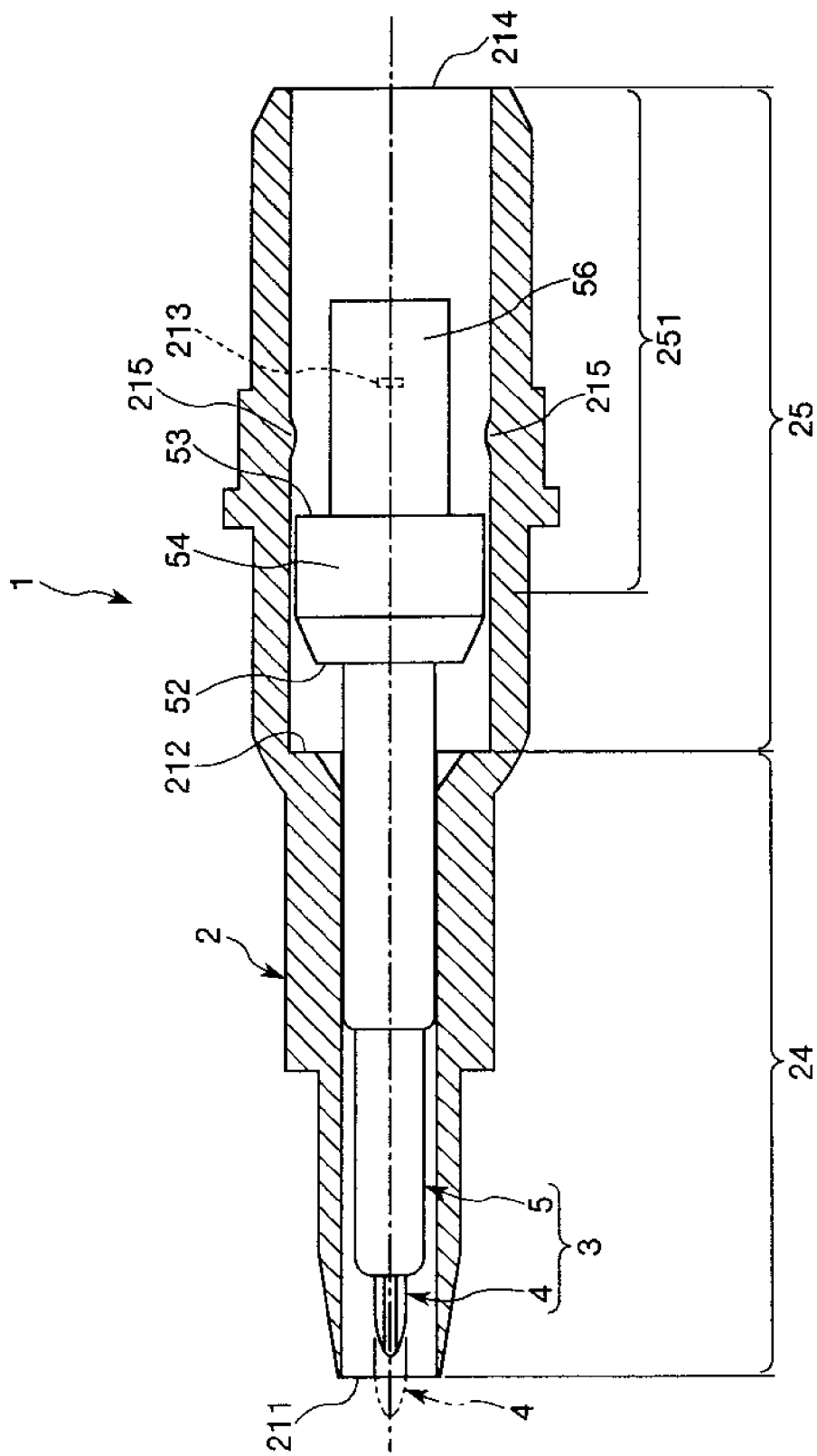
FIG. 1 is a partially longitudinal sectional view showing a first embodiment of a puncture device according to the present invention.
Figure 2:
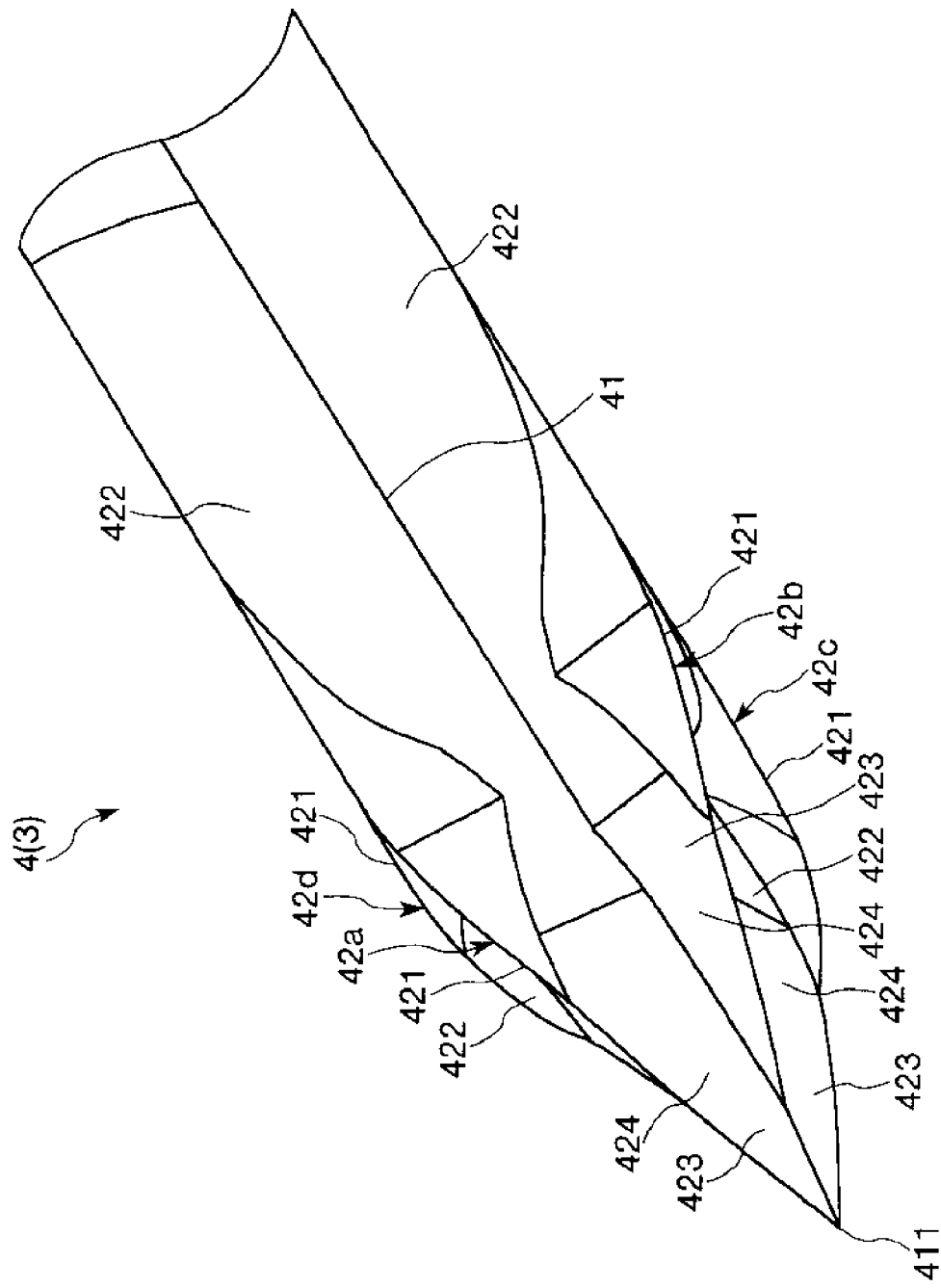
FIG. 2 is a diagrammatic perspective view showing a puncture needle (the first embodiment of the puncture needle of the present invention) provided with the puncture device shown in FIG. 1.
Figure 3:
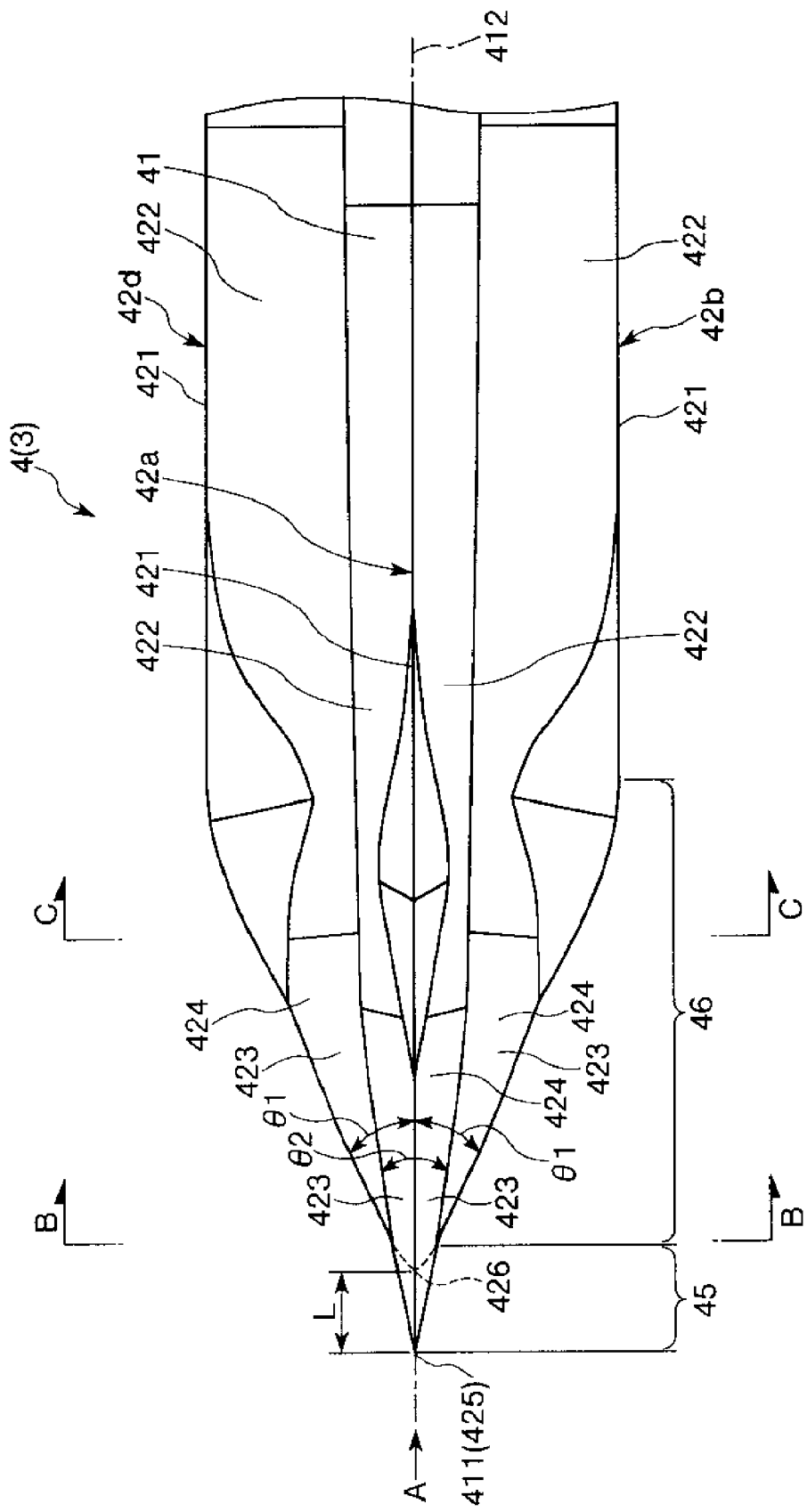
FIG. 3 is a side view showing the puncture needle shown in FIG. 2.
Figure 4:
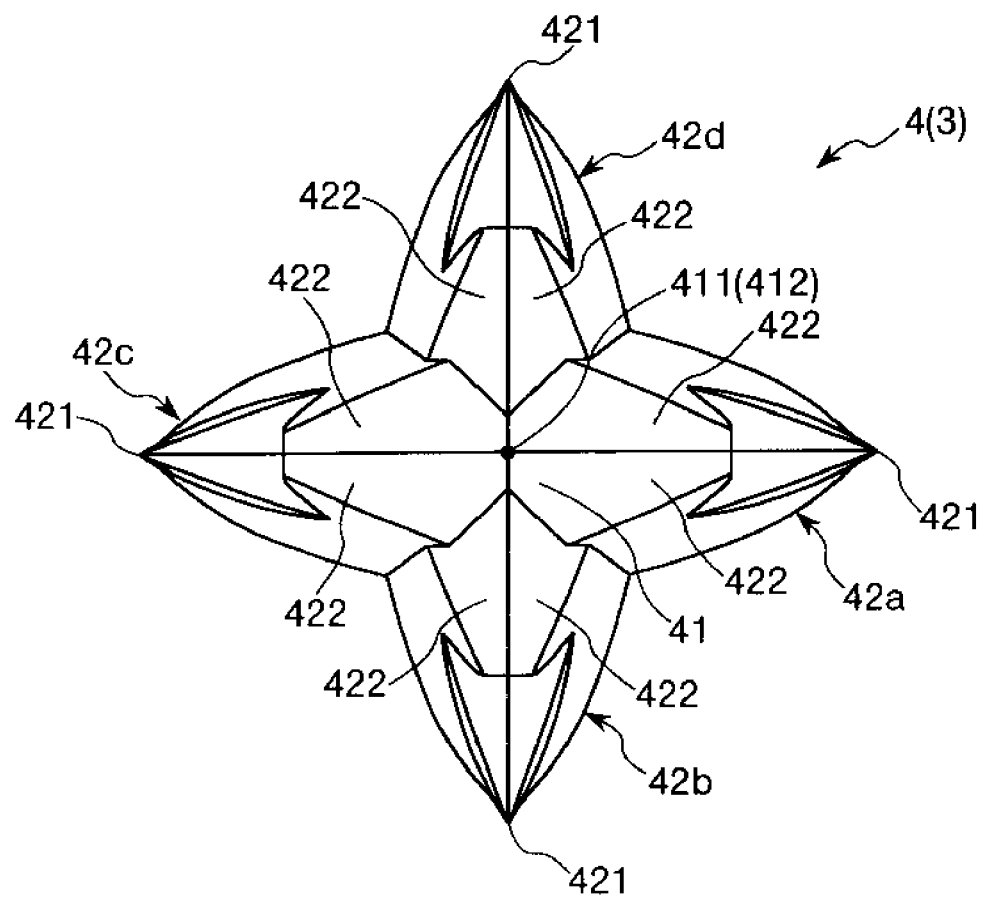
FIG. 4 is a view (diagrammatic elevational view) in which the puncture needle in FIG. 3 is seen from a direction of the arrow A.
Figure 5:
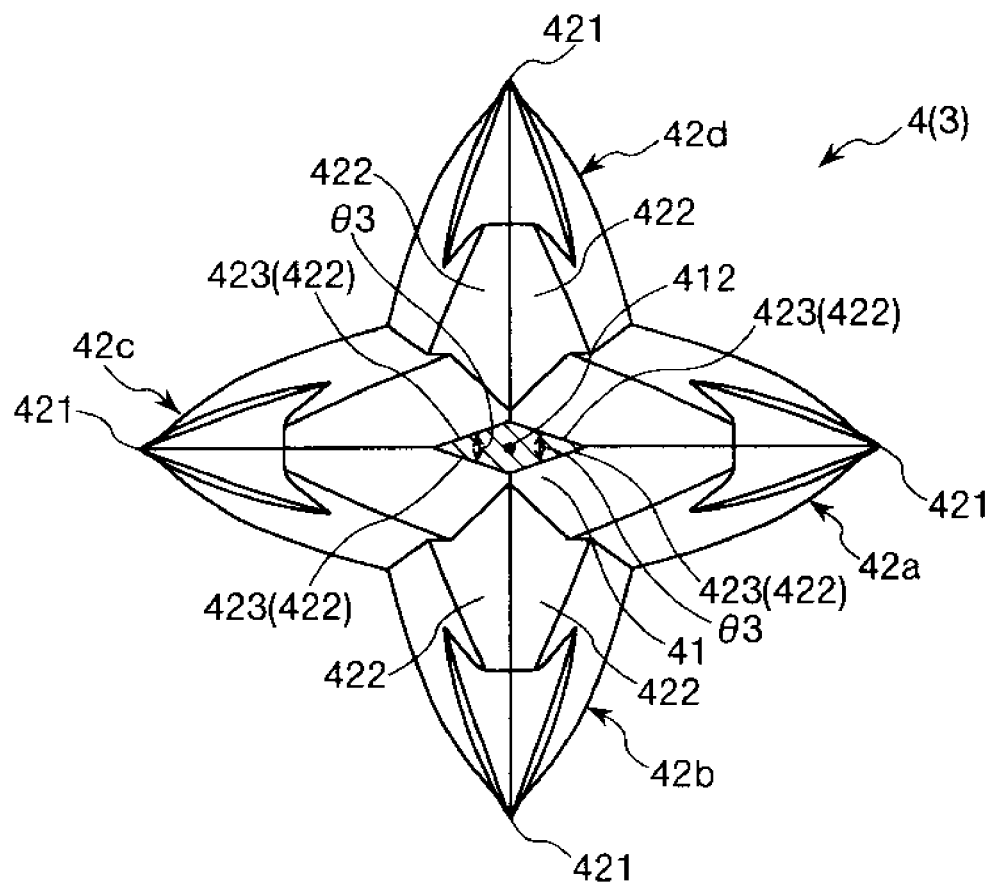
FIG. 5 is a sectional view taken along the line B-B in FIG. 3.
Figure 6:
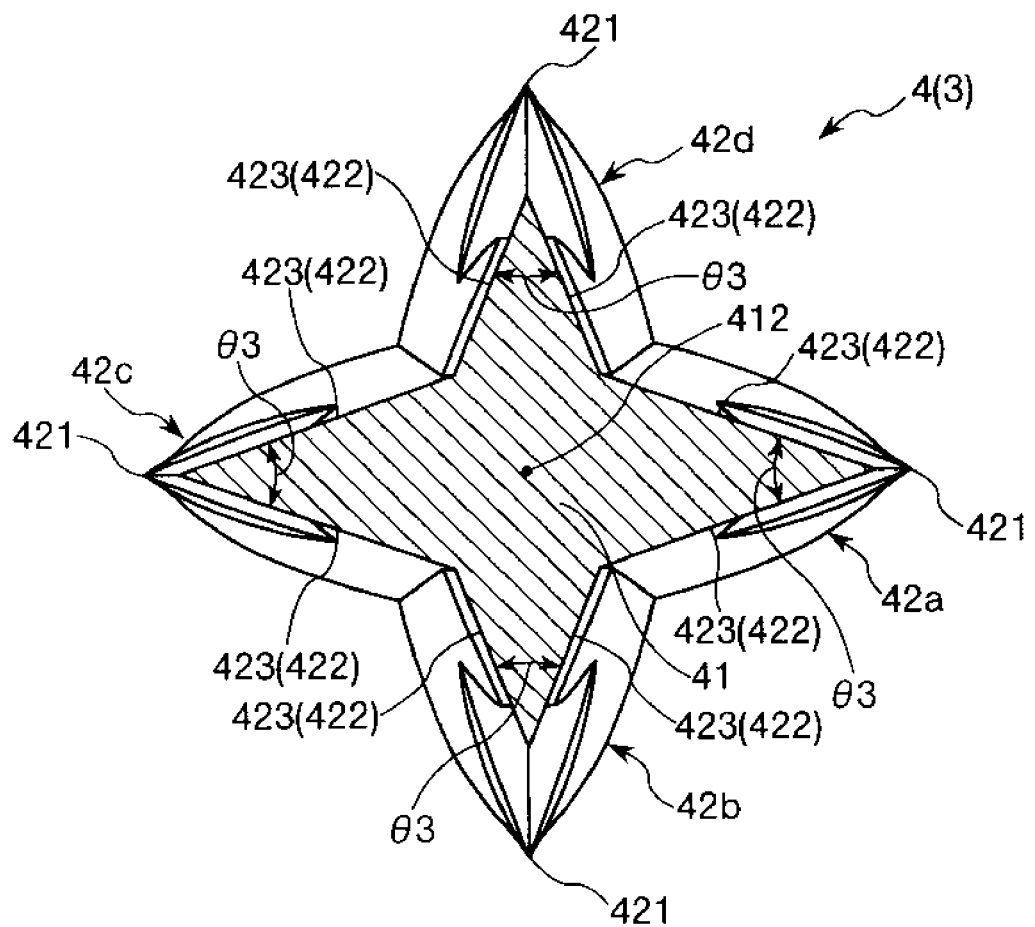
FIG. 6 is a sectional view taken along the line C-C in FIG. 3.
Figure 7:
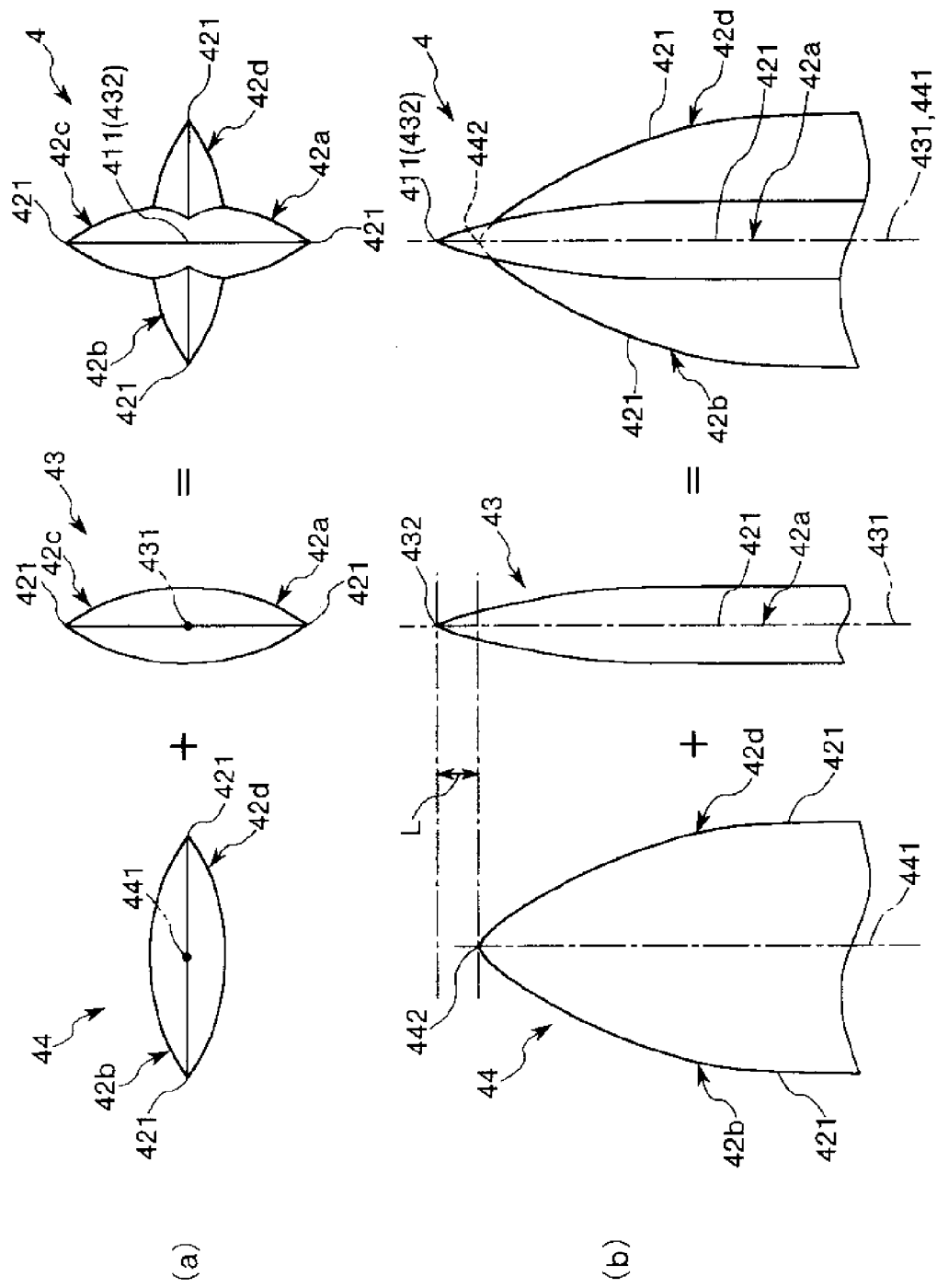
FIG. 7 is a schematic illustration view ((a) is a diagrammatic elevational view and (b) is a side view) for designing the puncture needle shown in FIG. 2.
Figure 8:
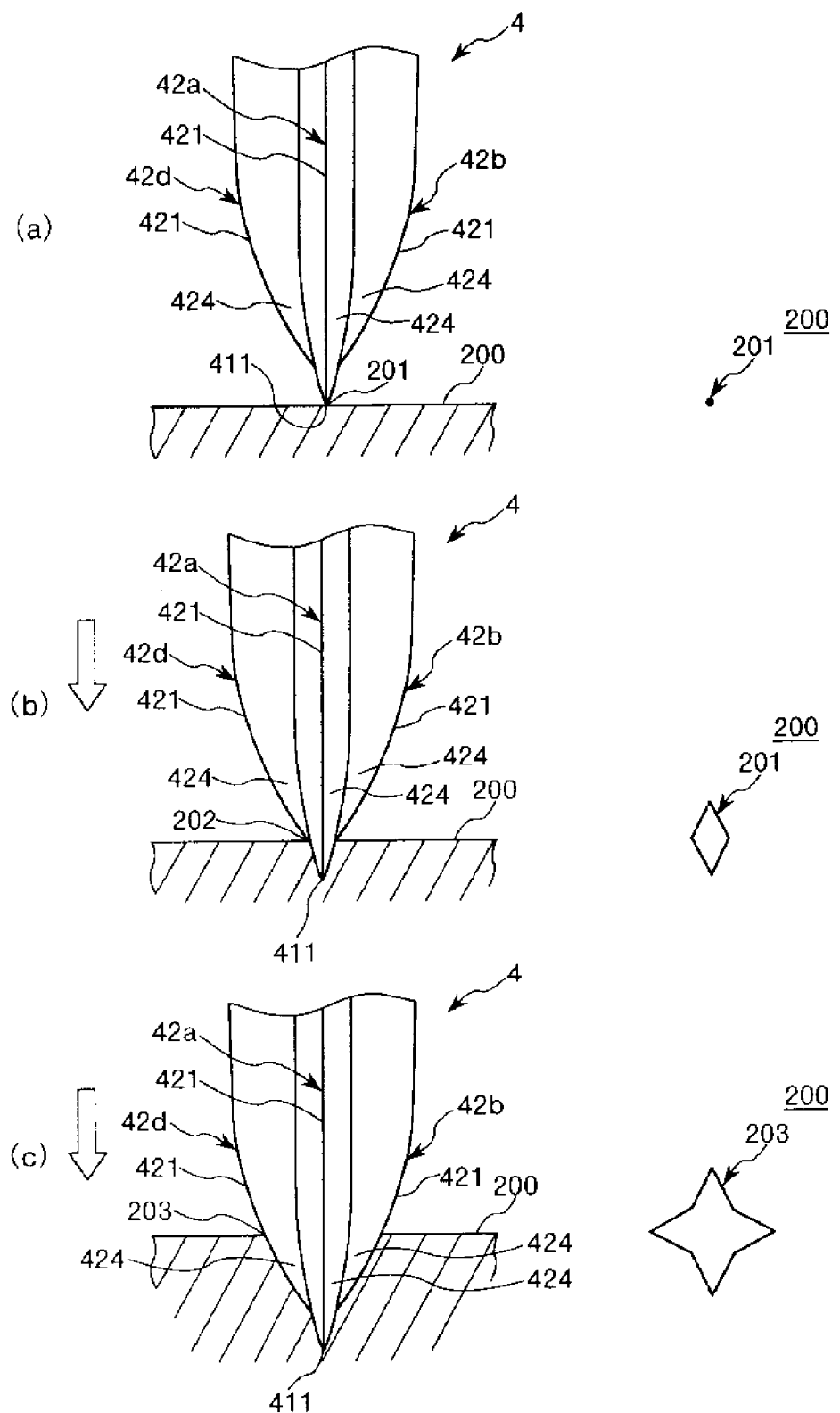
FIG. 8 is a view showing a state of puncturing by the puncture device shown in FIG. 1 (a figure in the left side is a partially longitudinal sectional view and a figure in the right side is a plan view showing a state of a wound site).
Figure 11:
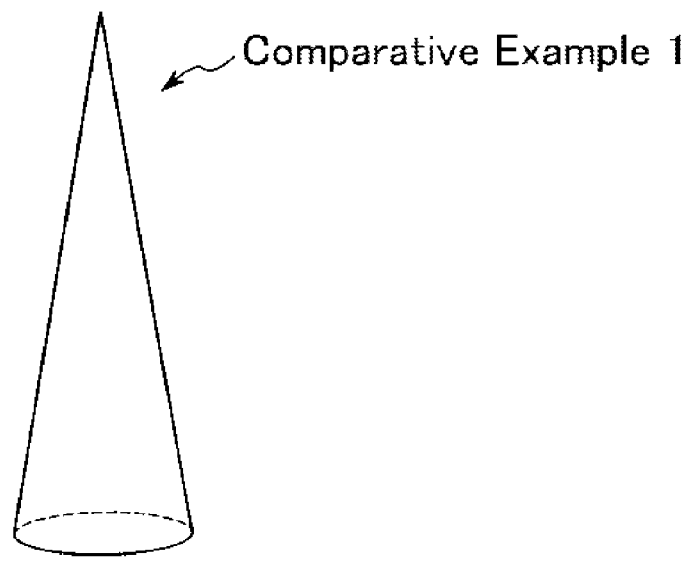
FIG. 11 is a diagrammatic perspective view showing a configuration of a puncture needle (needle body) of the Comparative Example 1.
Figure 12:
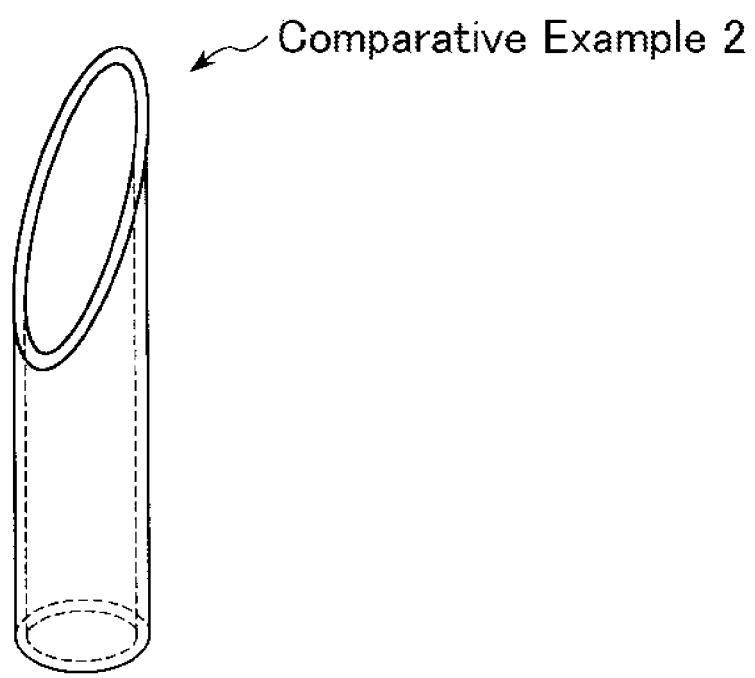
FIG. 12 is a diagrammatic perspective view showing a configuration of a puncture needle (needle body) of the Comparative Example 2.

FIG. 1 is a partially longitudinal sectional view showing a first embodiment of a puncture device according to the present invention. FIG. 2 is a diagrammatic perspective view showing a puncture needle (the first embodiment of the puncture needle of the present invention) provided with the puncture device shown in FIG. 1. FIG. 3 is a side view showing the puncture needle shown in FIG. 2. FIG. 4 is a view (diagrammatic elevational view) in which the puncture needle in FIG. 3 is seen from a direction of the arrow A. FIG. 5 is a sectional view taken along the line B-B in FIG. 3. FIG. 6 is a sectional view taken along the line C-C in FIG. 3. FIG. 7 is a schematic illustration view ((a) is a diagrammatic elevational view and (b) is a side view) for designing the puncture needle shown in FIG. 2. FIG. 8 is a view showing a state of puncturing by the puncture device shown in FIG. 1 (a figure in the left side is a partially longitudinal sectional view and a figure in the right side is a plan view showing a state of a wound site). In this regard, in the following, for convenience of the description, the left side and the right side in each of FIG. 1 and FIG. 3 will be referred to as a "distal end" and a "proximal end", respectively. Further, the left-lower side and the right-upper side in FIG. 2 will be referred to as a "distal end" and a "proximal end", respectively. Further, the upper side and the lower side in FIG. 7 (FIG. 11 and FIG. 12 are also the same as FIG. 7) will be referred to as a "distal end" and a "proximal end", respectively. Further, the lower side and the upper side in FIG. 8 are referred to as a "distal end" and a "proximal end", respectively.

The puncture device 1 shown in FIG. 1 is fitted to a puncture apparatus and then used (for example, "FINETOUCH (registered trademark)" produced by TERUMO Kabushiki Kaisha). The puncture device 1 has a casing (a puncture needle holder) 2 and a puncture needle 3 housed in the casing 2 so as to be movable in an axial direction of the casing 2. The casing 2 is composed of a tubular member. The puncture needle 3 is able to be divided into a needle body 4 for puncturing a biological surface 200, and a hub 5 supporting the needle body 4 and sliding inside the casing 2.

A distal end of the casing 2 is a part to come into contact with the biological surface 200 such as a fingertip, a humerus, a abdominal part, a femoral part and a lobe, and has an opening 211. As shown in FIG. 1, the needle body 4 of the puncture needle 3 is projected from the opening 211, thereby enabling the biological surface 200 to be punctured. Further, an opening 214 is formed at a proximal end of the casing 2.

Further, the casing 2 has a small diameter part 24 and a large diameter part 25, of which internal diameters are different from each other. The small diameter part 24 is positioned at a distal side with respect to the large diameter part 25.

The internal diameter of the large diameter part 25 of the casing 2 is constant in a zone 251. However, convex portions 215 are formed on an inner surface at substantially a central portion of the large diameter part 25. Thus, the convex portions 215 make contact with an enlarged diameter portion 54 of the hub 5. A proximal portion 56 of the hub 5 is relatively moved to a distal side of the casing 2 by engaging with the puncture mechanism of the puncture apparatus which is not shown in the drawings. As a result, the contacts between the convex portions 215 and the enlarged diameter part 54 of the hub 5 are released (a state shown in FIG. 1). Thus, the state is changed to a state that drive power of the puncture apparatus is transmitted on its own to the distal side of the zone 251 of the casing 2. In the case where the drive power is added, an end face 52 of the enlarged diameter part 54 of the hub 5 of the puncture needle 3 makes contact with a stepped portion 212 which is a boundary portion formed between the small diameter part 24 and the large diameter part 25 of the casing 2. By doing so, a maximum projecting length (maximum projecting amount) of the puncture needle 3 (needlepoint 411) from the opening 211 of the casing 2 is controlled.

Further, a pair of protrusions 213 and 213, which can engage with the enlarged diameter part 54 of the hub 5 of the puncture needle 3, is formed on an inner peripheral surface of the large diameter part 25 of the casing 2 (In FIG. 1, only one of the pair of protrusions 213 and 213 is drawn). The enlarged diameter part 54 is latched together the protrusions 213. By doing so, it is possible to prevent the puncture needle 3 from being removed from a proximal side of the casing 2.

The puncture needle 3 is capable of moving between a position that the end face 52 of the enlarged diameter part 54 is in contact with the stepped portion 212 and a position that an end face 53 of the enlarged diameter part 54 is in contact with the protrusions 213 in the casing 2 in an axial direction of the casing 2.

The puncture needle 3 is constituted from the needle body 4 and the hub 5.

The needle body 4 can be exposed at a distal side of the hub 5. As shown in FIG. 2, the needle body 4 has a main body and four cutting parts 42a, 42b, 42c and 42d which are provided so as to project from the main body 41.

The main body 41 is formed into a long (columnar)-like shape and a part to be a core of the needle body 4. Further, the main body 41 has a sharp needlepoint 411 at a distal end thereof. This needlepoint 411 makes it possible to puncture the biological surface 200.

As shown in FIG. 4 to FIG. 6, the cutting parts 42a to 42d are arranged at equiangular intervals (90-degrees intervals) around a central axis 412 of the main body 41, respectively. Since the cutting parts 42a to 42d are the same shape as each other, hereinafter, a description will be made on the cutting part 42a as a representative.

The cutting part 42a projects from an outer circumference of the main body 41 to a direction perpendicular to the central axis 412 (outer circumference direction). Further, the cutting part 42a extends along a direction of the central axis 412. A thickness of such a cutting part 42a, namely a distance between side surfaces 422 of the cutting part 42a is gradually decreased toward a direction to be far from the central axis 412. Consequently, a sharp cutting edge 421 is formed at a tip portion (peak (edge)) of the cutting part 42a. As described later, the cutting edge 421 makes it possible to make an incision on the biological surface 200 by originating on a part (wound 201) of the biological surface 200 punctured by the needlepoint 411 (referred to FIG. 8). In this regard, a curvature radius of the cutting edge 421 (a curvature radius of the needlepoint 411 is the same as that) is not particularly limited, but is preferably lower than 0.1 mm and more preferably lower than 0.05 mm.

As shown in FIG. 2 and FIG. 3, not only a height but also a thickness of a distal portion 424 of the cutting part 42a is gradually decreased toward a distal direction thereof from the central axis. For these reasons, the cutting part 42a is continuously formed with the needlepoint 411. In this regard, a gradually decreased ratio of the height of the distal portion 424 of the cutting part 42a, that is, an angle θ1 in FIG. 3 is not particularly limited, but is preferably in a range of 5 to 30 degrees and more preferably in a range of 10 to 20 degrees. Further, a gradually decreased ratio of the thickness of the distal portion 424 of the cutting part 42a, that is, an angle θ2 in FIG. 3 is not particularly limited, but is preferably in a range of 10 to 45 degrees and more preferably in a range of 18 to 33 degrees.

As shown in FIG. 5 and FIG. 6, it is preferred that at least side surfaces 423 of the distal portion 424 of the cutting part 42a are formed into a plate-like shape. An angle θ3 between the side surfaces 423 (ridge lines) (referred to FIG. 5 and FIG. 6) is not particularly limited, but for example, is preferably in a range of 10 to 45 degrees and more preferably in a range of 20 to 30 degrees.

In this regard, as shown in FIG. 4 to FIG. 6, both side surfaces of a part at a proximal side of the cutting part 42a are slightly curved toward an outward of the cutting part 42a compared with the side surfaces 423 of the distal portion 424 formed into the plate-like shape.

As shown in FIG. 2 to FIG. 4, in the needle body 4, the cutting part 42a and the cutting part 42c are arranged on an opposite side to each other through the central axis 412 to make a pair thereof, and the cutting part 42b and the cutting part 42d are arranged on the opposite side to each other through the central axis 412 to make a pair thereof. As shown in FIG. 3, a position of an intersection 425 (a position of the needlepoint 411) between lines extended from the cutting edges 421 (tip portion) to the distal directions of the cutting part 42a and the cutting part 42c is located at the distal side with respect to a position of an intersection 426 between lines extended from the cutting edges 421 to the distal directions of the cutting part 42b and the cutting part 42d. In other words, the position of the intersection 425 and the position of the intersection 426 are shifted to each other in the direction of the central axis 412.

By such an arrangement, in the needle body 4, a number (forming number or existing number) of the cutting parts in the cross-section shown in FIG. 5 becomes two (cutting parts 42a and 42c) and a number of the cutting parts in the cross-section shown in FIG. 6 becomes four (cutting parts 42a to 42d). That is, the number of the cutting parts at a cutting edge portion 45 in the vicinity of the needlepoint 411 of the needle body 4 is different from the number of the cutting parts at a needlepoint base portion 46 of the needle body 4 (referred to FIG. 3).

By this configuration, the cutting parts 42a and 42c can make an incision on the biological surface 200 prior to the cutting parts 42b and 42d at the time of making the incision on the biological surface 200 with the cutting parts 42a to 42d. In other words, when the cutting parts 42a to 42d make the incision on the biological surface 200, first of all, the cutting parts 42a and 42c make the incision on the biological surface 200, and then the cutting parts 42b and 42d with the cutting parts 42a and 42c make the incision on the biological surface 200. As described above, it is possible to make the incision on (cut into) the biological surface 200 in a stepwise fashion (time difference).

In this regard, a shift distance L between the position of the intersection 425 and the position of the intersection 426 is not particularly limited, but is preferably lower than 0.2 mm and more preferably in a range of 0.05 to 0.1 mm.

The needle body 4 (puncture needle 3) having the configuration described above makes it possible to puncture the biological surface 200. Next, a description will be made on the puncture while referring to FIG. 8.

As shown in FIG. 8(a), first, the needlepoint 411 of the needle body 4 is in contact with the biological surface 200. This makes it possible to puncture the biological surface 200 with the needlepoint 411 of the needle body 4 prior to making an incision on the biological surface 200 with the cutting parts 42a to 42d (cutting edges 421). At that time, a minute wound 201 is made on the biological surface 200 by the puncture with the needlepoint 411.

Thereafter, as shown in FIG. 8(b), the needle body 4 is pushed in a distal direction. Consequently, the needle body 4 punctures the biological surface 200 more deeply compared with the state shown in FIG. 8(a). Further, a pair (a set) of cutting parts 42a and 42c in the cutting parts 42a to 42d of the needle body 4 makes an incision on the biological surface 200 in an up-down direction in the drawing by originating on the wound 201. Thus, as shown in FIG. 8(b), a wound 202 is made into a straight line-like shape.

As described above, the cutting parts 42a and 42d are continuously formed with the needlepoint 411. This makes it possible to rapidly move to an operation of making the incision on the biological surface 200 with the cutting parts 42a and 42d after the biological surface 200 is punctured by the needlepoint 411.

As shown in FIG. 8(c), the needle body 4 is further pushed in the distal direction. Consequently, the needle body 4 punctures the biological surface 200 more deeply compared with the state shown in FIG. 8(b). Further, the cutting parts 42b and 42d in addition to the cutting parts 42a and 42c of the needle body 4 make an incision in the biological surface 200 in a left-right direction on the drawing. Thus, as shown in FIG. 8(c), a wound 203 is made into an across shape.

Thereafter, the needle body 4 is pulled in a proximal direction (back away from the biological surface 200).

By the steps as described above, it is completed that the biological surface 200 is punctured by the needle body 4.

As described above, the cutting parts 42a to 42d of the needle body 4 are arranged at the equiangular intervals around the central axis 412. Therefore, it is possible to make an incision on the biological surface 200 in a radial fashion. Further, when the needle body 4 makes the incision on the biological surface 200 in the radial fashion, the needle body 4 makes the incision on the biological surface 200 in the stepwise fashion as described above. Therefore, an area of making the incision on the biological surface 200 is expanded in the stepwise fashion. In contrast, in the case where the biological surface 200 is simply punctured by a conically-shaped needle body (hereinafter, referred to as "conventional needle body"), only a pinhole-shaped wound is made on the biological surface 200. In this case, depending on the depth thereof, there is a possibility that blood does not flow out from a wound site of the pinhole-shaped wound. Therefore, in the case where the biological surface 200 is punctured in the same depth as the depth of the pinhole-shaped wound obtained by using the conventional needle body, it is possible for the needle body 4 to more greatly puncture the biological surface 200 compared with the conventional needle body. As a result, it is possible for the blood to reliably flow out from the biological surface 200.

Further, in the conventional needle body, the biological surface 200 has to be punctured so that the blood flows out from the biological surface 200. This tends to deeply puncture the biological surface 200. Therefore, the conventional needle body produces increased pain at the time of the puncture. On the other hand, the needle body 4 performs not only the puncture by the needlepoint 411 but also the incision on the biological surface 200 by the cutting parts 42a to 42d. This makes it possible for the blood to reliably flow out from the biological surface 200 while suppressing the biological surface 200 from being deeply punctured (even the puncture is relatively shallow).

As described above, the needle body 4 is capable of achieving a purpose of reliably puncturing the biological surface 200 so that the blood flows out from the biological surface 200 and another purpose of preventing or suppressing the pain from being increased at the time of the puncture, which are an opposite purpose to each other.

Further, the needle body 4 is designed as follows. A description will be made on the needle body 4 while referring to FIG. 7.

As shown in FIG. 7, the needle body 4 is designed by combining two plate members 43 and 44 formed into an elongated plate-like shape, for example, on the CAD.

The thickness of the plate member 43 is gradually decreased toward a direction away from the central axis 431. This forms the cutting parts 42a and 42c (cutting edges 421) at both edges (longitudinal edges) of plate member 43. Further, the width of a distal portion of the plate member 43 is gradually decreased toward a distal direction, which is formed into a gradually decreased shape.

The thickness of the plate member 44 is gradually decreased toward the direction away from the central axis 441. This forms the cutting parts 42b and 42d (cutting edges 421) at both edges (longitudinal edges) of plate member 44. Further, the width of a distal portion of the plate member 44 is gradually decreased toward a distal direction, which is formed into the gradually decreased shape.

The central axis 431 of the plate member 43 is overlapped with the central axis 441 of the plate member 44. In this state, one of the plate members 43 and 44 is rotated 90 degrees around the central axis with respect to the other. Further, one (the plate member 44 in FIG. 7) of the plate members 43 and 44 is shifted to the other (the plate member 43 in FIG. 7) in only the shift distance L to the proximal side along the central axis 441. As a result, a distal end 442 of the plate member 44 is positioned (buried) into the plate member 43, so that only a distal end 432 of the plate member 43 is exposed. Thus exposed distal end 432 of the plate member 43 constitutes the needlepoint 411 of the needle body 4. In this regard, it is to be noted that the distal end 432 of the plate member 43 corresponds to the intersection 425 described above and the distal end 442 of the plate member 44 corresponds to the intersection 426.

By combining the plate member 43 and the plate member 44 as described above, it is possible to obtain the needle body 4 which is formed so as to integrally combine the plate member 43 and the plate member 44.

In the puncture needle 3, the needle body 4 is constituted of a resin material such as a thermoplastic resin. Further, the hub 5 is constituted of the resin material such as the thermoplastic resin or various kinds of metal material such as a stainless steel and the like. In the case where the needle body 4 and the hub 5 are constituted of the resin material, it is possible to obtain the puncture needle 3 in which the needle body 4 and the hub 5 are integrally formed. In this case, the needle body 4 and the hub 5 can be simultaneously formed, for example, by an injection molding method and the like. On the other hand, in the case where the needle body 4 is constituted of the resin material and the hub 5 is constituted of the metal material, it is possible to obtain the puncture needle 3 by separately forming the needle body 4 and the hub 5 and then connecting the separately formed needle body 4 and the hub 5 to each other.

Examples of the resin material include, but not particularly limited thereto, a polyolefin such as polyethylene (PE), polylactic acid (PLA), polypropylene (PP), an ethylene-propylene copolymer, an ethylene-vinyl acetate copolymer (EVA) and the like; a cyclic polyolefin (COP); a cyclic polyolefin copolymer (COC); a modified polyolefin; polyvinyl chloride; polyvinylidene chloride; polystyrene (PS); a polyamide; a polyimide; a polyamideimide; a polycarbonate (PC); poly-(4-methylpenten-1), an ionomer; an acrylic-based resin; polymethyl methacrylate; an acrylonitrile-butadiene-styrene copolymer (ABS resin); an acrylonitrile-styrene copolymer (AS resin); a butadiene-styrene copolymer; polyoxymethylene; polyvinyl alcohol (PVA); an ethylene-vinylalcohol copolymer (EVOH); a polyester such as polyethylene terephthalate (PET), polybuthylene terephthalate (PBT), polycyclohexane terephthalate (PCT), polyethylene naphthalate (PEN) and the like; a polyether; a polyether ketone (PEK); a polyether ether ketone (PEEK); a polyether imide; a polyacetal (POM); a polyphenylene oxide; a modified polyphenylene oxide; a polysulfone; a polyether sulfone; a polyphenylene sulfide (PPS); a polyallylate; an aromatic polyester (liquid crystal polymer); a fluorine-based resin such as polytetrafluoroethylene, polyvinylidene fluoride and the like; various kinds of thermoplastic elastomer such as a styrene-based thermoplastic elastomer, a polyolefin-based thermoplastic elastomer, a polyvinyl chloride-based thermoplastic elastomer, a polyurethane-based thermoplastic elastomer, a polyester-based thermoplastic elastomer, a polyamide-based thermoplastic elastomer, a polybutadiene-based thermoplastic elastomer, a trans polyisoprene-based thermoplastic elastomer, a fluorocarbon rubber-based thermoplastic elastomer, a chlorinated polyethylene-based thermoplastic elastomer and the like; a copolymer, a blend compound and a polymer alloy of these materials as a main component; and the like. One or more of these materials may be used independently or in combination.

Among the resin materials, particularly, a flexural modulus thereof (defined in the ASTMD 790) is preferably 2000 MPa or more and more preferably in a range of 2000 to 25000 MPa. Further, a flexural strength thereof (defined in the ASTMD 790) is preferably 50 MPa or more and more preferably in a range of 80 to 300 MPa. Further, a hardness thereof (Shore R hardness M scale) is preferably in a range of 50 to 150 and more preferably in a range of 70 to 130. By using the resin materials meeting such conditions as a constituent material of the needle body 4, it is possible to reliably prevent disadvantages such as unintentionally bends and damages of the needle body 4 from occurring when the biological surface 200 is punctured by the needle body 4.

Among the resin materials, examples of the resin materials of which the flexural modulus, the flexural strength and the hardness fall within the above ranges include: the polylactic acid and the cyclic polyolefin. The polylactic acid has biodegradability. Therefore, even if fragments of the needle body 4 remain in the wound 203 (in a living body), adverse affects to the living body are prevented. Further, the polylactic acid and the cyclic polyolefin have no toxicity. Therefore, even if the fragments of the needle body 4 remain in the wound 203 (in the living body), the adverse affects to the living body are prevented.

Second Embodiment

Figure 9:
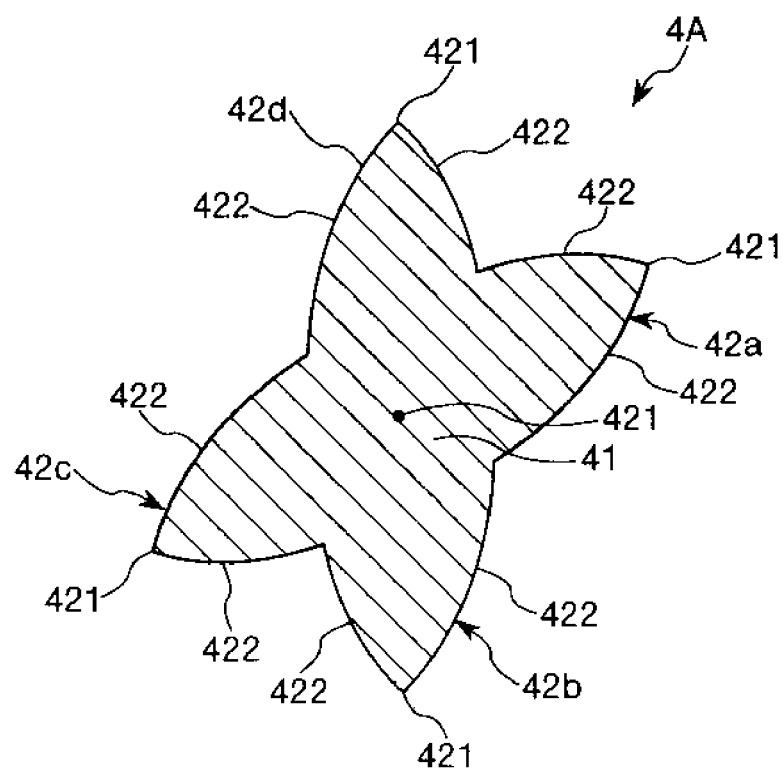
FIG. 9 is a cross-section view showing a second embodiment of a puncture needle according to the present invention.

FIG. 9 is a cross-section view showing a second embodiment of a puncture needle according to the present invention.

Hereinafter, a description will be made on a second embodiment of a puncture needle and a puncture device according to the present invention with reference to the drawing. However, the description of the second embodiment will be focused on the points differing from the puncture needle and the puncture device of the first embodiment described above, and the puncture needle and the puncture device of the second embodiment which are common with the first embodiment are omitted.

The present embodiment is the same as the first embodiment, except that positions to form four cutting parts are different from those of the first embodiment.

In the needle body 4A shown in FIG. 9, the cutting parts 42a to 42d are arranged around the central axis 412. However, an angle between the adjacent two cutting parts is different from that between the other adjacent two cutting parts. The angle between the cutting part 42a and the cutting part 42b is 150 degrees. The angle between the cutting part 42b and the cutting part 42c is 30 degrees. The angle between the cutting part 42c and the cutting part 42d is 150 degrees. The angle between the cutting part 42d and the cutting part 42a is 30 degrees.

Such a needle body 4A makes it possible to reliably bleed.

Third Embodiment

Figure 10:
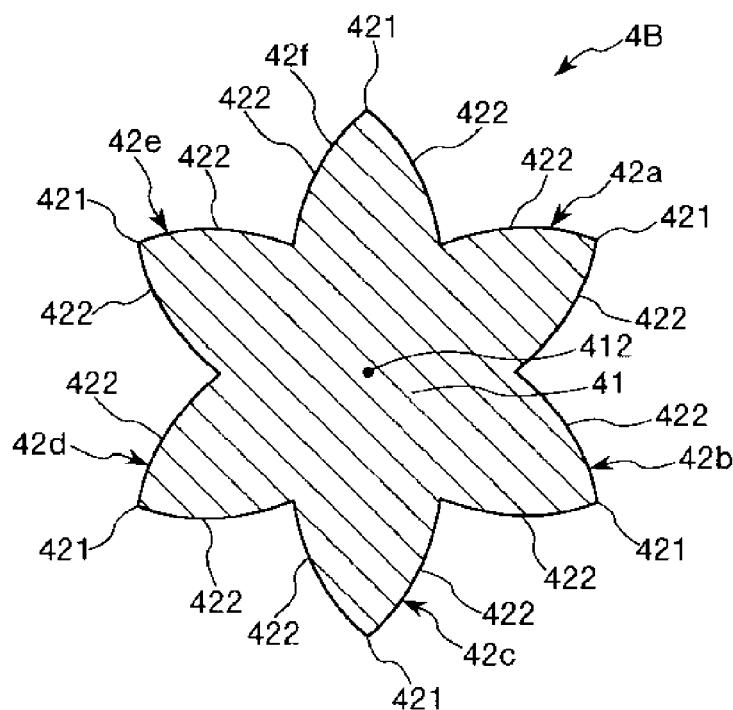
FIG. 10 is a cross-section view showing a third embodiment of a puncture needle according to the present invention.

FIG. 10 is a cross-section view showing a third embodiment of a puncture needle according to the present invention.

Hereinafter, a description will be made on a third embodiment of a puncture needle and a puncture device according to the present invention with reference to the drawing. However, the description of the third embodiment will be focused on the points differing from the puncture needles and the puncture devices of the first and second embodiments described above, and the puncture needle and the puncture device of the third embodiment which are common with the first and second embodiments are omitted.

The present embodiment is the same as the first embodiment, except that a number of cutting parts is different from that of the first embodiment.

The needle body 4B shown in FIG. 10 has six cutting parts 42a to 42f. These cutting parts 42a to 42f are arranged at the equiangular intervals (30 degrees intervals) around the central axis 412.

A number of the cutting parts of such a needle body 4B is larger than that of the cutting parts of the needle body 4 of the first embodiment. Accordingly, an area to make an incision on the biological surface 200 is expanded. Such a needle body 4B makes it possible to reliably flow the blood from the biological surface 200 when the biological surface 200 is punctured by the needle body 4B. Further, it is easy to stop bleeding.

As described above, although the puncture needle and the puncture device according to the present invention have been described above based on the embodiments illustrated in the drawings, the present invention is not limited thereto. Each part constituting the puncture needle and the puncture device may be replaced with an arbitrary part exhibiting the same function as described above. Further, if necessary, one or more arbitrary constituent object may be added to the puncture needle and the puncture device according to the present invention.

Further, the number of the cutting parts of the puncture needle is not limited to four or six, for example, may be three, five, or seven or more.

EXAMPLES

Hereinafter, a description will be made on concrete examples of the present invention.

Example 1

A puncture device configured as shown in FIG. 1 and like was produced. Specifications of the puncture device are as follows.
Constituent materials of the needle body and the hub: polylactic acid (flexural strength: 90 MPa, flexural modulus: 7000 MPa, and hardness: 120 (Shore R hardness M scale))
Angle θ1: 17 degrees
Angle θ2: 27 degrees
Angle θ3: 24 degrees
Shift distance L: 0.1 mm
Constituent material of the casing: polypropylene Example 2

A puncture device configured as shown in FIG. 1 and like was produced in the same manner as the Example 1, except that the constituent material of the needle body was changed to a cyclic polyolefin (flexural strength: 100 MPa, flexural modulus: 2200 MPa, and hardness: 80 (Shore R hardness M scale)).

Comparative Example 1

A puncture device configured as shown in FIG. 1 and like was produced in the same manner as the Example 1, except that a shape of the needle body was changed into a conular-like shape (referred to FIG. 11) and the constituent material of the needle body was change to a polylacitc acid (flexural strength: 90 MPa, flexural modulus: 7000 MPa, and hardness: 120 (Shore R hardness M scale)).

Comparative Example 2

A puncture device configured as shown in FIG. 1 and like was produced in the same manner as the Example 1, except that the needle body was changed to a hollow needle (referred to FIG. 12) and the constituent material of the needle body was change to a stainless steel (SUS304).

Each puncture device was loaded to a puncture apparatus, "FINETOUCH (registered trademark)", produced by TERUMO Kabushiki Kaisha, and then sides of left index fingers of six subjects were punctured. Thereafter, a degree of pain caused by use of each of the puncture devices and a degree of bleeding were evaluated according to the following criteria including four grades.

In this regard, the puncture apparatus was set so that a speed of the distal end of the puncture needle at the time of reaching to skin became 3 m/second, and a puncture depth was set to 2.0 mm.

(Degree of Pain)
◎: Absolutely no pain
○: Degree of feeling that the distal end of the puncture needle makes contact with the biological surface (so painless)
Δ: Slightly pain
×: Significantly pain (Degree of Bleeding)
◎: The subjects bled in a sufficient amount to measure a blood sugar level.
○: The subjects bled slightly (the subjects bled in a degree of no problem to measure the blood sugar level (an amount thereof was lower than an amount in the grade "◎" of the degree of bleeding)).
Δ: The subjects bled in an insufficient amount to measure the blood sugar level.
×: The subjects did not bleed at all.

These results are shown in Table 1.

TABLE 1

| | | Evaluation | | | |
|---|---|---|---|---|---|
| | | Ex. 1 | Ex. 2 | Com. Ex. 1 | Com. Ex. 2 |
| Subject 1 | Degree of Pain | ◎ | ◎ | X | Δ |
| | Degree of Bleeding | ◎ | ◎ | X | ○ |
| Subject 2 | Degree of Pain | ○ | ◎ | X | ○ |
| | Degree of Bleeding | ◎ | ◎ | X | X |
| Subject 3 | Degree of Pain | ◎ | ◎ | X | Δ |
| | Degree of Bleeding | ◎ | ◎ | Δ | X |
| Subject 4 | Degree of Pain | ○ | ○ | X | Δ |
| | Degree of Bleeding | ◎ | ◎ | Δ | ○ |
| Subject 5 | Degree of Pain | ◎ | ◎ | X | Δ |
| | Degree of Bleeding | ○ | ◎ | X | ○ |
| Subject 6 | Degree of Pain | ◎ | ◎ | X | Δ |
| | Degree of Bleeding | ○ | ○ | ○ | Δ |

As is clear from Table 1, in both the Examples 1 and 2, it was possible to obtain the blood of the sufficient amount to measure the blood sugar level while suppressing the pain at the time of puncturing.

In contrast, in the Comparative Examples 1 and 2, although it depended on the subjects, it was impossible to obtain the blood of the amount needed to measure the blood sugar level, and the subjects involved significant pains.

Further, the constituent materials of the needle body and the hub used in the Example 1 were changed to other thermoplastic resin. Then, a puncture device including a needle body and hub using such a thermoplastic resin was evaluated in the same manner as the Example 1. The results were the same results as the Examples 1 and 2.

Further, the angle $\theta_1$ of the needle body used in the Example 1 was changed within a range of 10 to 20 degrees. Then, a puncture device having such an angle $\theta_1$ was evaluated in the same manner as the Example 1. The results were substantially the same results as the Examples 1 and 2.

Further, the angle $\theta_2$ of the needle body used in the Example 1 was changed within a range of 18 to 33 degrees. Then, a puncture device having such an angle $\theta_2$ was evaluated in the same manner as the Example 1. The results were substantially the same results as the Examples 1 and 2.

Further, the angle $\theta_3$ of the needle body used in the Example 1 was changed within a range of 20 to 30 degrees. Then, a puncture device having such an angle $\theta_3$ was evaluated in the same manner as the Example 1. The results were substantially the same results as the Examples 1 and 2.

Further, the shift distance L of the needle body used in the Example 1 was changed within a range of 0.05 to 0.1 mm. Then, a puncture device having such a shift distance L was evaluated in the same manner as the Example 1. The results were substantially the same results as the Examples 1 and 2.

INDUSTRIAL APPLICABILITY

A puncture needle according to the present invention is constituted of a resin material. Such a puncture needle comprises an elongated main body having a sharp needlepoint at a distal end thereof and at least three cutting parts provided so as to project from the elongated main body to a direction perpendicular to a central axis of the elongated main body, extending along the central axis, and arranged around the central axis. Adjacent cutting parts in the three cutting parts are arranged so as to shift to each other in a direction of the central axis, so that the adjacent cutting parts make an incision on a biological surface in a time difference. Therefore, when the biological surface is punctured, the needle body performs both the puncture by the needlepoint and the incision on the biological surface by the cutting parts. This becomes it possible for the blood to reliably flow out from the biological surface. Further, when the biological surface is punctured, the performance of the incision on the biological surface by the cutting parts makes wound to be made on the biological surface large. Therefore, the blood reliably flows out from the biological surface without setting to an excessively-large puncture depth. As described above, it is possible to prevent the puncture depth from becoming excessively large, thereby preventing or suppressing the pain at the time of puncturing the biological surface. Accordingly, the puncture needle according to the present invention has industrial applicability.

What is claimed is:

1. A puncture needle constituted of a resin material, the puncture needle comprising:
    an elongated main body having a sharp needlepoint at a distal end thereof; and
    at least three cutting parts provided so as to project from the elongated main body to a direction perpendicular to a central axis of the elongated main body, extending along the central axis, and arranged around the central axis,
    wherein each of the at least three cutting parts has a distal portion and a proximal side with respect to the distal portion, and both side surfaces of at least a part of the proximal side are curved in an outward direction with respect to the cutting part and convexly curved with respect to the central axis, and wherein adjacent cutting parts in the at least three cutting parts are arranged so as to be disposed in different positions with respect to the central axis, so that the adjacent cutting parts make an incision on a biological surface in a time difference.

2. The puncture needle as claimed in claim 1, wherein a height of the distal portion from the central axis is gradually decreased toward a distal direction thereof.

3. The puncture needle as claimed in claim 1, wherein the at least three cutting parts include an even number of cutting parts, these cutting parts are arranged at equiangular intervals around the central axis, and a height of the distal portion of each cutting part from the central axis is gradually decreased toward a distal direction thereof, wherein the cutting parts include one pair of cutting parts positioned so that they are opposite to each other through the central axis and other pair of cutting parts than the one pair of cutting parts, wherein each of the cutting parts of the one and other pairs has a tip portion, a position with respect to the central axis of an intersection between lines extended from the tip portions of the one pair of cutting parts toward the distal direction thereof is different from a position with respect to the central axis of an intersection between lines extended from the tip portions of the other pair of cutting parts toward the distal direction thereof.

4. The puncture needle as claimed in claim 1, wherein a flexural modulus (defined in an ASTMD790) of the resin material is 2000 MPa or more.

5. The puncture needle as claimed in claim 1, wherein a flexural strength (defined in an ASTMD790) of the resin material is 50 MPa or more.

6. The puncture needle as claimed in claim 1, wherein a hardness (Shore R hardness M scale) of the resin material is in a range of 50 to 150.

7. A puncture device comprising:

the puncture needle defined in claim 1; and a casing housing the puncture needle therein so as to be movable.

* * * * *